United States Patent [19]

Hoff

[11] Patent Number: Plant 7,232

[45] Date of Patent: May 22, 1990

[54] LILY PLANT NAMED PENNY LANE

[75] Inventor: Petrus M. M. Hoff, Hemmerbuurt, Netherlands

[73] Assignee: Hoffgaarde B.V., Netherlands

[21] Appl. No.: 350,236

[22] Filed: May 11, 1989

[51] Int. Cl.[5] ..... A01H 5/00

[52] U.S. Cl. ..... Plt./68

[58] Field of Search ..... Plt. 68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new lily plant named Penny Lane particularly characterized by its light pink flowers, floriferous habit, early flowering, and good retention.

1 Drawing Sheet

The present invention comprises a new and distinct cultivar of lily, botanically known as Lilium (Asiatic hybrid), and hereinafter referred to by the cultivar name Penny Lane.

Penny Lane is a product of a planned breeding program which had the objective of creating new lily cultivars with long strong stems, bright petal color, short greenhouse time, and strong characteristics while in the vase.

Penny Lane was originated by me from a hybridization made in a controlled breeding program in Hem, The Netherlands beginning in 1984. Both the female parent and the male parent of Penny Lane were unknown seedlings.

Penny Lane was discovered and selected by me as one flowering plant within the progeny of the stated cross in June 1986 in a controlled environment in Hem, The Netherlands.

I accomplished the first act of asexual reproduction of Penny Lane by the taking of bulbils of the initial selection in September 1986 in a controlled environment in Hem. Horticultural examination of selected units initiated in June 1988 has demonstrated that the combination of characteristics as herein disclosed for Penny Lane are firmly fixed and are retained through successive generations of asexual reproduction.

Penny Lane has not been observed under all possible environmental conditions. The phenotype may vary significantly with variations in environment such as temperature, light intensity, and day length. The following observations, measurements, and comparisons describe plants grown in Hem, The Netherlands under greenhouse conditions which approximate those generally used in commercial practice.

The following traits have been repeatedly observed and are determined to be basic characteristics of Penny Lane which in combination distinguish this lily as a new anddistinct cultivar.

1. The plant height is approximately 100 cm.
2. No leaf burning.
3. There are many flowers in bloom at one time.
4. Size 9–10 produces four flowers.
5. Early flowering.
6. Good flower retention.

The accompanying photographic drawing shows typical flower characteristics of Penny Lane, with colors being as true as possible with illustrations of this type.

In the following description, color references are made to The Royal Horticultural Society Colour Chart (R.H.S.). The color values were determined at approximately 8:00 a.m. on June 25, 1988 under cloudy conditions at Hem, The Netherlands.

Origin: Seedling.

Name: Penny Lane.

Parentage:

*Female parent.*—Unknown seedling.

*Male parent.*—Unknown Seedling.

*Classification.*—Asian hybrid.

Ploidy: Diploid.

Plant:

1. *Plant height (on opening of the anthers of the first flower).*—Short to medium.
2. *Stalk.*—Anthocyanin coloring — absent. Color: dark green. Growth of Hair: absent. Type of coat of hair: long. Internode length: average and uniform. Cross section: rounded. Bulbils: present, on parts above soil level. Color of the bulbils: purple.
3. *Leaf.*—Arrangement alternate. Top angle of the base with the stalk: weakly acute. Length: medium. Width: medium. Thickness: normal. Form (middle-third part of the stalk): elliptic. Color of the top: dark green. Luster of the top: very weak. Growth of hair at the bottom: lacking. Top: acute. Curve of the edge: lacking. Membraneous edge: lacking. Indentation of the edge: lacking. Form in cross section: flat. Top part: incurved. Flexibility: medium.

Flower:

1. *Structure.*—Type: umbellate. Secondary flowers: absent. Growth of hair: absent. Bracts: few. Number of bracts in comparison with the number of primary flowers: fewer. Bracteole: absent. Position: erect. Type: flat. Diameter: medium. Cross-section: medium. Height of crown: medium. Length of longest flower stalk: medium.
2. *Petal.*—Length of longest exterior petal: medium. Width of widest exterior petal: medium to narrow. Length of longest interior petal: medium. Width of widest interior petal: medium to narrow. Color of the inside of the interior petal: 65D. Color of the outside of the interior petal: 65D. Color of the inside of the exterior petal: 65D. Color of the outside of the exterior petal: 65D. Marking on the inside: present. Color of the marking: 166A. Type of marking on the inside: spots. Density of the spots in the marking: relatively sparse. Color of the inside of the throat: near 180C. Color of the outside of the throat: 65D. Texture of the inside: smooth. Luster at the inside: present. Curvature of petals: present, weak, entire petal. Curve of the edges of the petal: none.Bended part of the petals: entire. Extent of bending: weak.

Reproductive Organs:

*Length of stamens.*—Short.
*Color of the filaments.*—White.
*Colors of the anthers.*—Reddish Brown.
*Color of pollen.*—Dark Brown.
*Length of pistil.*—Medium.
*Color of the style.*—White.
*Color of the stigma.*—Brown.

Bulb:

*Type (in dormant season).*—Type 4
*Top.*—Rounded
*Formation of new bulbs.*—Concentric
*Length and width of scales.*—Medium
*Density of Scales.*—Dense
*Color of the exterior scales.*—White
*Top of the scales.*—Pointed
Underground part of the stalk.—Bulblets — present.

I claim:

1. A new and distinct cultivar of lily plant named Penny Lane, as illustrated and described.

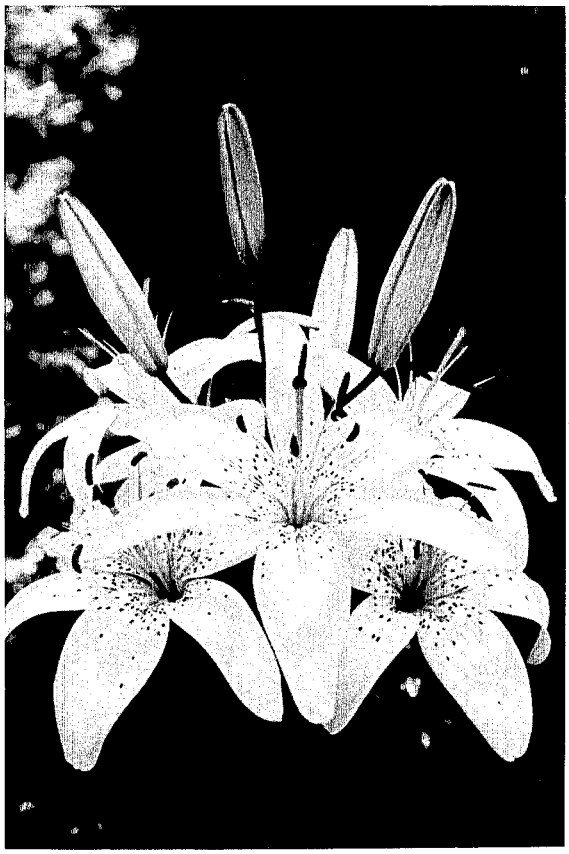

* * * * *